United States Patent [19]
Räsänen

[11] Patent Number: 5,879,308
[45] Date of Patent: Mar. 9, 1999

[54] PROCEDURE FOR MEASURING A PATIENT'S IMPEDANCE

[75] Inventor: Taisto Räsänen, Helsinki, Finland

[73] Assignee: Instrumentarium Oy, Helsinki, Finland

[21] Appl. No.: 12,301

[22] Filed: Jan. 23, 1998

Related U.S. Application Data

[63] Continuation-in-part of Ser. No. 653,501, May 24, 1996, abandoned.

[51] Int. Cl.⁶ .................... A61B 5/08; A61B 5/04
[52] U.S. Cl. .................... 600/536; 600/547; 600/513
[58] Field of Search .................... 600/536, 547, 600/506, 509, 513

[56] References Cited

U.S. PATENT DOCUMENTS

| | | |
|---|---|---|
| 3,677,261 | 7/1972 | Day . |
| 3,742,936 | 7/1973 | Blanie et al. . |
| 3,784,908 | 1/1974 | Anderson . |
| 3,882,851 | 5/1975 | Sigworth .................... 600/536 |
| 4,038,975 | 8/1977 | Vrana et al. . |
| 4,540,002 | 9/1985 | Atlas .................... 600/547 |
| 4,805,261 | 2/1989 | Heinze et al. . |
| 4,917,099 | 4/1990 | Stice . |
| 4,919,145 | 4/1990 | Marriott . |
| 4,953,556 | 9/1990 | Evans . |
| 4,993,423 | 2/1991 | Stice .................... 600/547 X |
| 5,170,794 | 12/1992 | Reiche . |
| 5,309,917 | 5/1994 | Wang et al. . |

FOREIGN PATENT DOCUMENTS

| | | |
|---|---|---|
| 249823 | 12/1987 | European Pat. Off. . |
| 2186652 | 1/1974 | France . |
| 2113248 | 10/1971 | Germany . |
| 2949887 | 6/1981 | Germany . |

Primary Examiner—Francis J. Jaworski
Attorney, Agent, or Firm—Andrus, Sceales, Starke & Sawall

[57] ABSTRACT

The present invention relates to a procedure for measuring a patient's impedance. Based on the impedance, it is possible to monitor the patient's respiration and/or blood circulation. In the procedure, a plurality of electrodes (1a, 1b; 1d, 2; 2a) are connected to be patient and the changes in the impedance relationships between the electrodes (1a, 1b, 2) are measured. The invention makes it possible to use the same measuring conductors and measuring electrodes for impedance measurement as are used in ECG measurement.

38 Claims, 5 Drawing Sheets

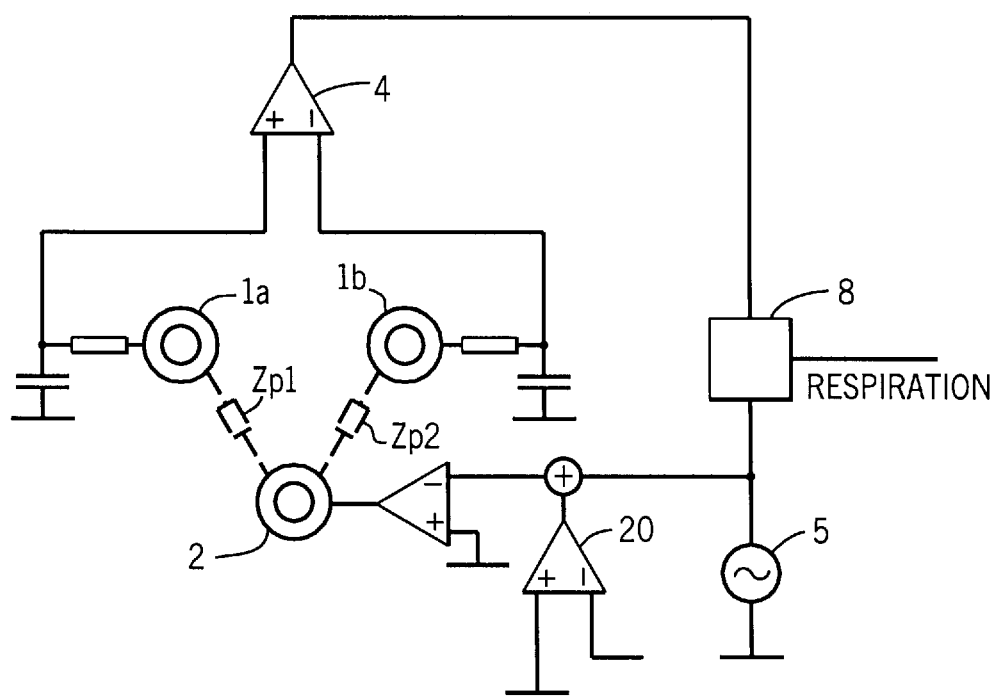

PROCEDURE FOR MEASURING A PATIENT'S IMPEDANCE

CROSS REFERENCE TO RELATED APPLICATIONS

The present application is a continuation-in-part application of U.S. application Ser. No. 08/653,501, filed May 24, 1996, and now abandoned.

BACKGROUND OF THE INVENTION

The present invention relates to a procedure for the measurement of the impedance of a patient.

An impedance method is used to measure a patient's respiration and blood circulation, such as cardiac stroke volume, cardiac output, cardiac contractility indices, thoracic fluid content, deep vein thrombosis, peripheral blood flow, and arterial occlusive disease.

Impedance respiration measurement, i.e. respiration measurement by the aid of a variable impedance, is based on the measurement of changes in electric conductivity in the chest. Electric conductivity decreases during inhalation as air flows into the lungs, air having a low electric conductivity, and increases during exhalation as air is discharged from the lungs.

The measurement is generally performed using a highfrequency, constant nominal value current as measuring current, so that the impedance of the chest can be calculated from the voltage set up across it. In this case, the chest impedance is mainly resistive, with a reactive component of only about 15%. Measured with a 100 kHz signal, the resistance of the chest generally has a magnitude of about 20–60 ohms. Respiration only causes a change of approximately 0.1–1 ohm in the resistance, because most the measuring current does not flow through the highly resistive lung tissue but through the muscles and the back.

In addition, the measurement is disturbed by the stray capacitances of the cables and amplifier, although these only have a minor significance because the voltage generated across them is in a different phase relative to the voltage generated by the resistive component of the impedance of the chest.

A high-frequency measuring current is used because the impedance of the electrodes decreases with increasing frequency. The skin-electrode impedance decreases to one hundredth when the measurement signal is increased from a low frequency to 100 kHz. In practice, the upper limit for the measuring signal frequency is about 100 kHz, because at higher signal frequencies too much of the measuring current begins to flow through stray capacitances. The measuring frequencies used are generally in the range of 10–100 kHz.

In impedance measurements previously known, two or more electrodes are used. When the measurement is performed using two electrodes, the measuring current has to be supplied via the same electrodes as are used for the measurement itself. This results in a measurement error, because the current density is larger in the vicinity of the current supply electrodes, and the impedance changes occurring in the tissue near the current supply electrodes appear larger in relation to those occurring in the rest of the tissue. Moreover, the non-linearity of the current density in the tissue causes error in the measurement result.

In practical monitoring, however, the biggest drawback with two-electrode measurement is that the impedances of the electrodes and measuring cables are summed with the chest impedance, with the result that the small change in chest impedance caused by respiration easily gets lost in the total impedance.

To correct the measurement errors referred to above, measuring procedures involving four or more electrodes have been developed. In a four-electrode procedure, the current is supplied to two outer electrodes and the measurement is performed with two inner electrodes. When the measuring amplifier has a high input impedance, the current flowing through the measuring electrodes, which causes the measurement error, is small. Besides, the impedances of the current supply cables and electrodes are not summed with the impedance to be measured. In addition, the measurement area can be located at a larger distance from the current supply electrodes, in which case the magnitude of the current density in the tissue in the area between the measuring electrodes is roughly constant. Moreover, the impedance changes in the area between the measuring electrodes appear larger in relation to the changes in other areas, making it possible to define the measurement area more precisely. In addition, the measurement area extends deeper into the tissue.

By using guard electrodes in addition, the error caused by the non-linearity of the current density can be reduced. By further increasing the number of electrodes used, the measurement area can be focused better and it is even possible to compute an impedance tomogram by means of a computer.

Since impedance respiration measurement in patient monitoring is generally performed simultaneously with ECG measurement using the ECG cable as the measuring cable, two-point measurement is generally used, because the monitors usually have three-wire ECG cables. This means that the above-described problems associated with two-point measurement cause disturbances in the measurement.

BRIEF SUMMARY OF THE INVENTION

The object of the present invention is to eliminate the problems described above.

A specific object of the present invention is to provide a new type of procedure for monitoring a patient's respiration.

A further object of the present invention is to provide a simple and reliable procedure for monitoring a patient's respiration, allowing respiration monitoring to be performed using the same measuring cables and electrodes as in ECG measurement As for the features characteristic of the present invention, reference is made to the claims.

In the procedure of the invention for measuring a patient's impedance, at least two, preferably three electrodes are connected to the patient. It is also possible to use more than three electrodes. According to the invention, the patient's respiration or blood circulation is monitored by measuring the changes in the impedance relationships between the electrodes.

One aspect of the procedure of the invention is that one, or more preferably more than one, impedance formed in the patient between electrode pairs is/are measured, one of said electrodes being a grounding electrode, on which the measurement is performed. In a preferred case, the change in the relation between the measured impedances is determined.

The procedure of the invention has the advantage that the measurement of a patient's respiration can be performed using the same measuring cables and electrodes as are used for ECG measurement.

A further advantage of the procedure of the invention is that the equal cable impedances and equal electrode impedances as well as equal tissue impedances cancel each other, so that carrier of the signal to be measured is small and the relative modulation produced in the carrier by respiration is therefore larger and thus easier to measure than in prior-art two-point measurement.

Furthermore, the procedure of the invention eliminates the earlier problems resulting from the measuring cable impedances being summed with the impedance to be measured, and no separate low-impedance respiration measurement cable is needed because the impedances cancel each other, but instead the normal ECG cable supplied by the monitor manufacturer can be used.

An additional advantage of the present invention as compared with prior art is that the procedure of the invention allows the impedance change to be determined more accurately and more reliably than in the earlier two-point measurement.

In an embodiment of the procedure of the invention, the electrodes are arranged asymmetrically relative to the lungs, so that the impedances between the electrodes will be affected differently by the alveolar air in the lungs. In addition, a measuring signal is fed into the patient through one of the electrodes and the modulation of the measuring signal caused by the inter-electrode impedances is determined. From the modulation, it is possible to conclude the change in the impedance relationship and further that air is flowing into or out of the patient's lungs, air having a poor electric conductivity.

In a preferred embodiment, a measuring signal is supplied via two electrodes, one of the electrodes is grounded with a grounding impedance, which may consist of a resistor, coil, capacitor or a combination of these, and the voltage appearing across the grounding impedance, the current flowing through the grounding impedance, or the phase of the voltage or current is measured. The measured signal is further compared with the measuring signal to determine its modulation.

In another aspect, the measuring signal can also be supplied via the grounding electrode to achieve the foregoing advantages.

In a preferred embodiment, the voltage of an individual electrode or the voltage difference between the electrodes can be measured, and, based on this measurement, the change in the impedance relationship between the electrodes can be determined.

In an embodiment of the present invention, a plurality of electrodes are connected to the patient. In this case, it is also possible to measure the relative change in the impedances appearing in the area between the electrodes in relation to each other. The measuring signal is preferably an a.c. signal having a frequency of about 10–100 kHz, preferably about 30 kHz. The measuring signal may be a voltage signal or a current signal.

BRIEF DESCRIPTION OF THE SEVERAL VIEWS OF THE DRAWING

In the following, the invention is described by the aid of embodiment examples by referring to the attached drawing, in which.

DETAILED DESCRIPTION OF THE INVENTION

Figure 2:
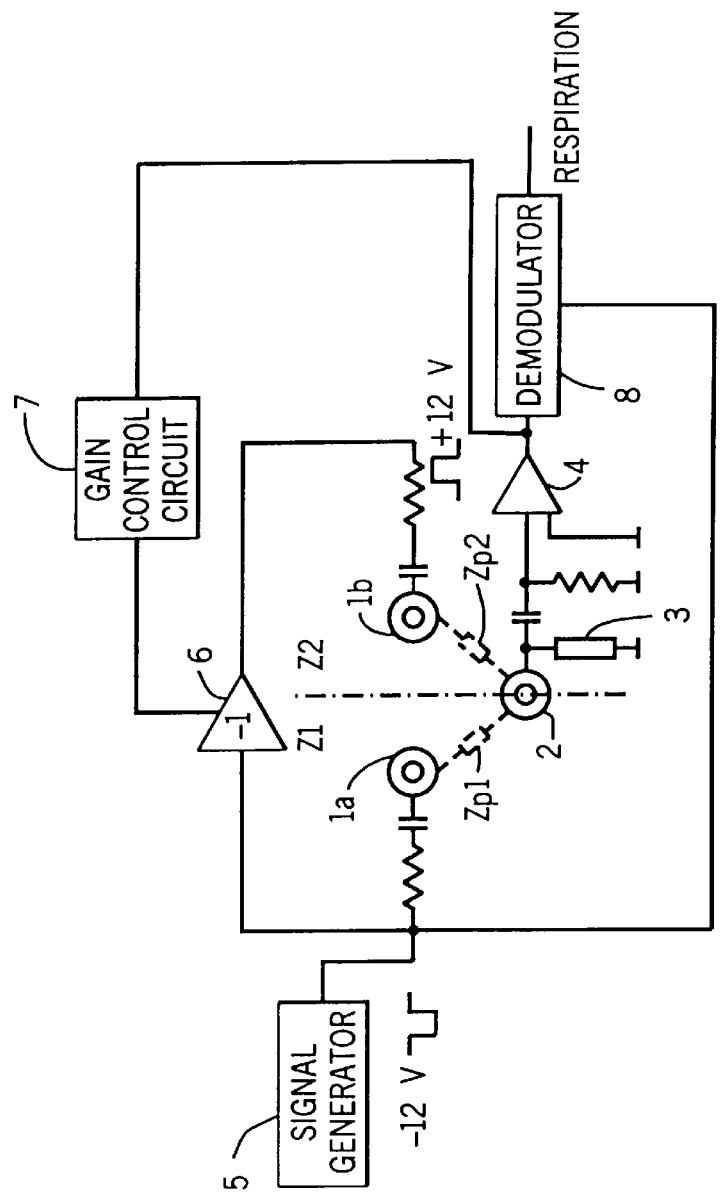
FIG. 2 presents a diagram representing an apparatus suitable for the procedure of the invention.
Figure 1:
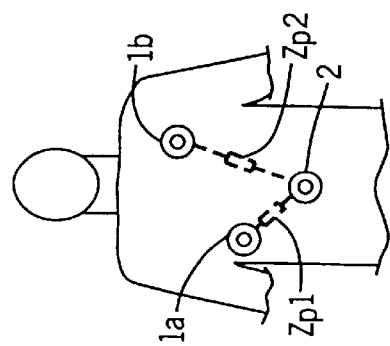
FIG. 1 illustrates the principle of implementation of a procedure as provided by the invention.

Referring to FIG. 1 and 2, the procedure of the present invention is applied to the measurement of a patient's respiration as follows. Electrodes 1a, 1b and electrode 2 are connected to the patient, preferably in the region of the lungs and asymmetrically relative to the lungs. As the respiration is monitored using the same measuring cables and electrodes as in ECG measurement, electrodes 1a and 1b correspond to the active electrodes in ECG measurement and electrode 2 to the neutral electrode in ECG measurement. FIG. 1 also presents the patient impedances Zp1 and Zp2 appearing between the electrodes. Between active electrode 1a and the neutral electrode 2, patient impedance Zp1 appears, and between active electrode 1b and the neutral electrode 2, patient impedance Zp2 appears.

Through the active electrodes 1a, 1b, a measuring signal in opposite phase is supplied, which may be e.g. a +/–12 V voltage signal having a frequency of 30 kHz. In the embodiment in FIG. 2, the measuring signal is supplied from a signal generator 5 directly to electrode 1a and via an inverter 6 to electrode 1b. When the body impedance remains unchanged and the impedances Z1 and Z2 on each side of the vertical broken line in FIG. 2 are approximately equal, the voltage across the grounding impedance 3, measured by means of amplifier 4, is approximately zero, because the voltages in opposite phase cancel each other. If this is not the case, the impedances Z1 and Z2 can be matched e.g. as follows. Referring to FIG. 2, matching can be achieved in the circuit in FIG. 2 by supplying an asymmetric bipolar measuring signal, in other words, by supplying one of the electrodes 1a, 1b with a smaller measuring signal than the other. In practice, the matching is performed e.g. by adjusting the gain of the amplifier acting as an inverter by means of a gain control circuit 7. The control circuit 7 is controlled by the output of the measuring amplifier 4. The purpose of the matching is to balance the unchanging components of the impedances so that the carrier produced by them at the measuring point is zero, permitting the relative modulation of the carrier of the measuring signal to be seen considerably more clearly, due to the change in the impedance relationship, than in prior-art solutions.

When the patient is breathing, he/she inhales air, which has a low electric conductivity, and if the active electrodes 1a, 1b have been suitably connected to the patient, the air has a different effect on impedance Zp1 than on impedance Zp2, thus having an effect on the impedance relationship Zp1/Zp2. The impedance change further affects the voltage across the grounding impedance 3, and this voltage is compared with the supply signal. Based on this voltage change, it is possible to establish the change in the impedance relationship and whether the patient is breathing or not.

Figure 4:
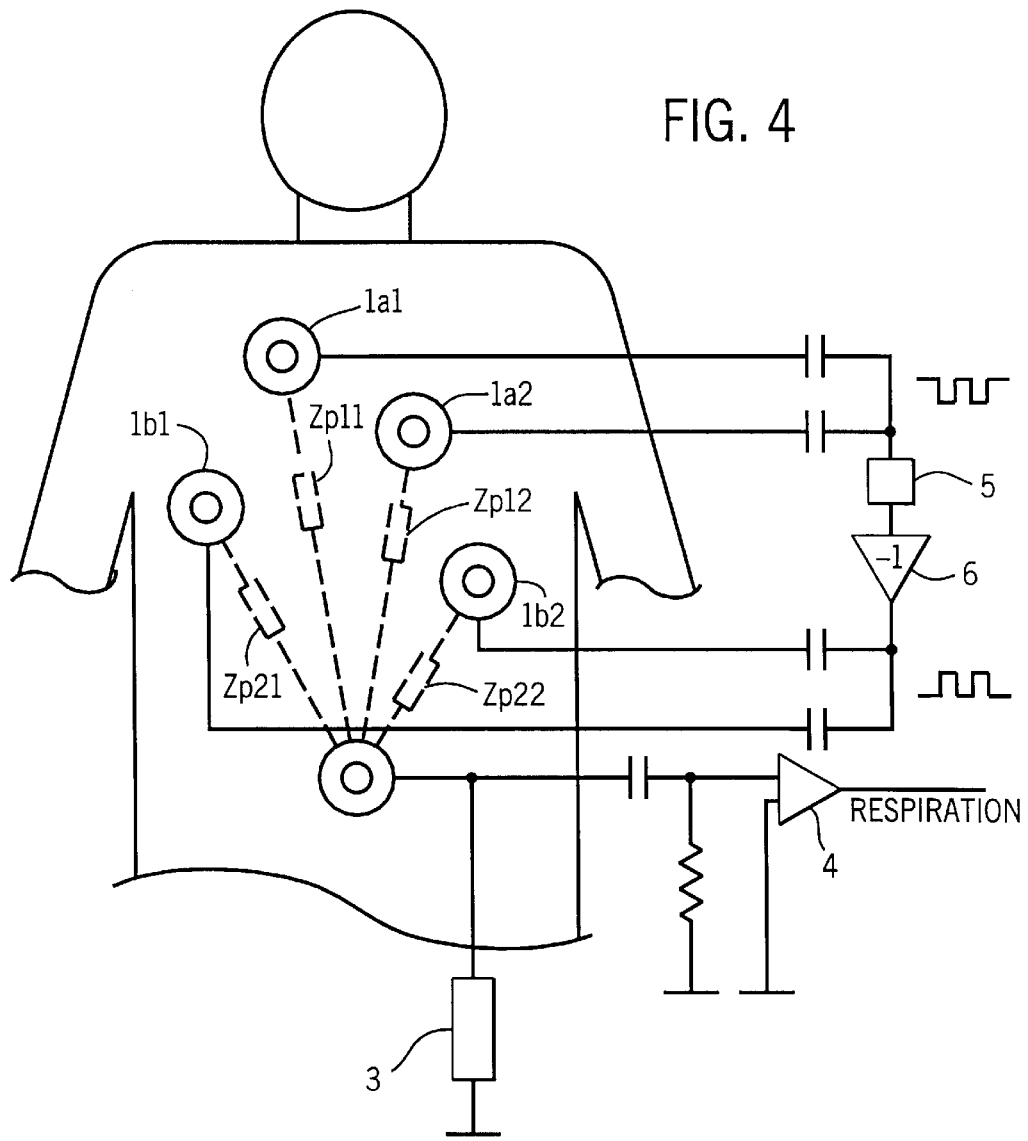
FIG. 4 presents a diagram representing an apparatus employing four electrodes.

Referring further to FIG. 1 and 2, possible apparatus for carrying out the invention are presented as a summary. The measuring signal generator may be either a current generator or a voltage generator, in other words, the measuring signal feed into the patient may be either a current signal or a voltage signal. Further, the measuring signal can be supplied to the electrodes either in unipolar or in bipolar form, i.e. either in opposite phase or in phase. In addition, the measuring signal can be supplied from one or more electrodes, and more than three electrodes can be used. FIG. 4 shows one such technique employing four electrodes. Components shown in FIG. 4 corresponding to those in FIG. 1 have similar or analogous reference numerals. Moreover, the measuring signal can be supplied via a resistor, capacitor, coil, transformer or a combination of these. The essential point in the procedure of the invention is that, by means of the measuring signal, the change in the relationship between impedances Z1 and Z2 is determined, said change being proportional to changes in the amount of alveolar air in the patient's lungs.

Figure 5A:
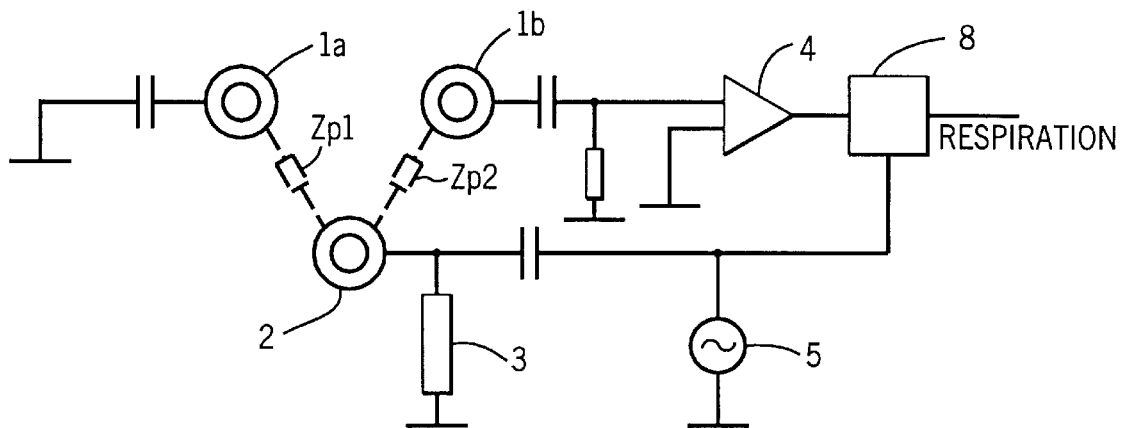
FIGS. 5A, B, and C present diagrams representing apparatus in which the measuring signal is supplied via the grounding electrode.

As noted above, the measuring signal can also be supplied via the grounding electrode 2. Techniques by which this may be accomplished are shown in FIG. 5 which is analogous to FIGS. 2 and 3 and in which similar components have been identified with the same or analogous reference numerals. One way in which this supply of the measuring signal may be accomplished is shown in FIG. 5A which corresponds to FIG. 2 and in which electrode 1a comprises an electrode used for EKG purposes. A further technique is shown in FIG. 5B in which electrodes 1a and 1b are both used for impedance measuring purposes.

Figure 5B:
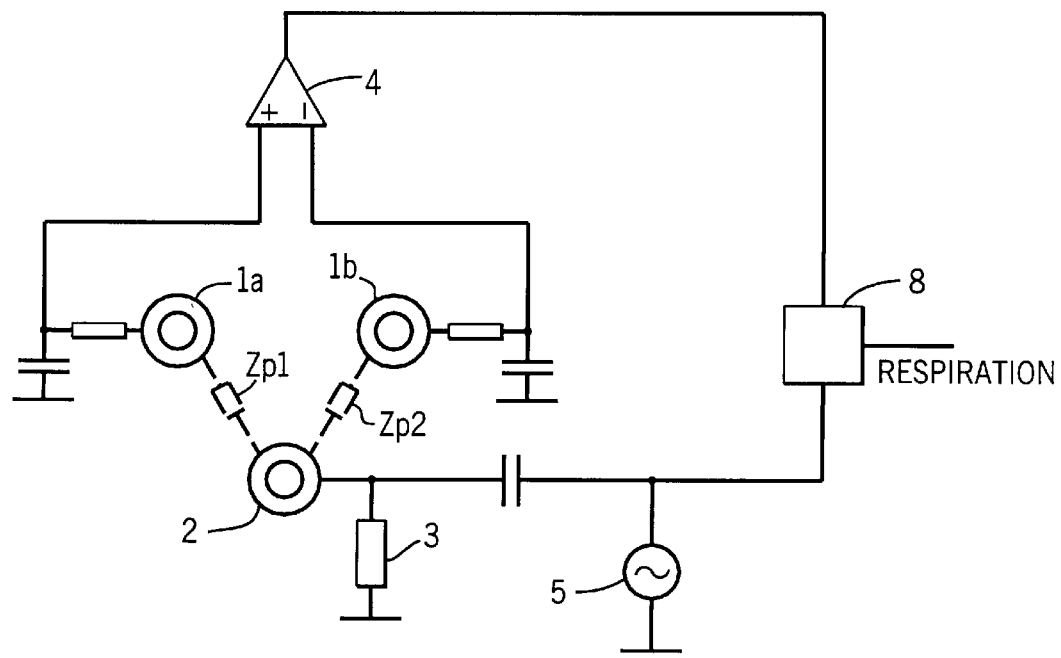

A still further modification of the technique shown in FIG. 5B is shown in FIG. 5C. As noted above, impedance respiration measurement is generally performed simultaneously with ECG measurement using the ECG electrodes. In one conventional form of electrocardiographic circuitry, a common mode amplifier 20 having one input connected to a circuit reference, which may be ground, and another input connected to one or more ECG leads, has its output connected to the right leg, or RL, electrocardiographic electrode so that the common mode amplifier attempts to drive the patient's body to the circuit reference. This provides improved common mode cancellation or rejection because the patient's body and the ECG circuit, in effect, share a common reference.

As shown in FIG. 5C, the measuring signal can be supplied to electrode 2 by adding same to the output of the common mode amplifier 20 in the RL drive circuit.

As noted above, the procedure of the invention can also be implemented using two electrodes so that the signal is supplied via one electrode while the other electrode is grounded with a grounding impedance. In this case, the voltage across the grounding impedance or the phase of the voltage or current is measured and compared with the measuring signal, whereupon the change in the patients impedance between the electrodes can be determined on the basis of this comparison.

Figure 3:
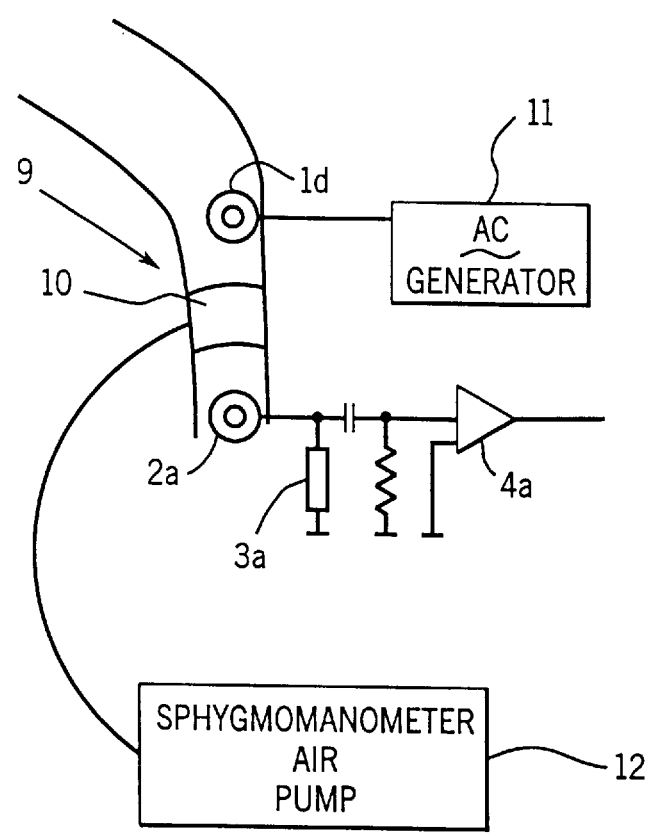
FIG. 3 presents a diagram representing an apparatus suitable for the procedure of the invention as used for monitoring a patient's blood circulation.

Referring to FIG. 3, the following is a description of the use of impedance measurement as provided by the invention for the monitoring of a patient's blood circulation, especially for determining the pulse volume curve based on the fact that bloodfilled tissue has a lower impedance. In FIG. 3, blood circulation in a patient's calf vein is being monitored. FIG. 3 shows part of the patient's leg 9, with the patient sitting e.g. on the edge of a bed. In FIG. 3, placed around the calf is a blood pressure cuff 10 which can be set tight around the calf by pumping air into it. The air is pumped into the cuff 10 by means of a pumping device 12 connected to it. Connected to the patient is an electrode id and a grounding electrode 2a, a measuring signal being supplied from an a.c. generator 11 via electrode 1d. As for the measurement of the impedance, reference is made to the description presented above by referring to FIG. 1 and 2.

This method aims at measuring venous reflux. When the valves in the veins are in good condition, there is less reflux. When air is pumped into the cuff, the blood flows away from the veins as the cuff exerts a pressure on them. When the cuff is deflated, the veins are refilled with blood. If the valves in the veins leak, then the veins are refilled more quickly and therefore the impedance change is faster than in the case of healthy valves.

The invention is not limited to the examples of its embodiments described above, but instead many variations are possible in the scope of the inventive idea defined by the claims.

It is recognized that other equivalents, alternatives, and modifications aside from those expressly stated, are possible and within the scope of the appended claims.

I claim:

1. A method for measuring a patient's impedance comprising the steps of:

connecting first and second electrodes to the patient at spaced locations on the skin of the patient;

connecting the second electrode to ground through a grounding impedance;

supplying a periodically varying measuring signal to the first electrode to provide an electrical signal through the patient's impedance to the second electrode and the grounding impedance, a characteristic of the electrical signal being determined by the impedance of the patient; and measuring an electrical characteristic at the grounding impedance resulting from the provision of the electrical signal to the grounding impedance to ascertain the impedance of the patient.

2. A method as defined in claim 1 wherein the measuring step is further defined as measuring at least one of the voltage across the grounding impedance, the current flowing through the grounding impedance, and a phase characteristic of the voltage or current resulting from the periodically varying measuring signal.

3. A method as defined in claim 1 wherein variations in the impedance of the patient alter the electrical signal characteristic, and wherein the measuring step is further defined as measuring changes in the electrical characteristic at the grounding impedance resulting from the altered electrical signal to ascertain variations in the impedance of the patient.

4. A method as defined in claim 3 wherein physiological functioning of the patient varies the impedance of the patient and wherein the method is further defined as a method for measuring the variations in the patient's impedance resulting from the physiological functioning of the patient.

5. A method as defined in claim 4 further defined as a method for measuring the variations of the patient's impedance resulting from the physiological functioning of the lungs of the patient and wherein the step of connecting the electrodes is further defined as connecting the electrodes at spaced locations having a desired orientation with respect to the position of the lungs in the body of the patient.

6. A method as defined in claim 5 further defined as a method for determining the variation of the patient's impedance resulting from the respiratory functioning of the lungs.

7. A method as defined in claim 6 wherein the connecting steps are further defined as connecting first and second ECG electrodes to the patient.

8. A method as defined in claim 1 wherein the measuring step is further defined as comparing the electrical characteristic at the grounding impedance to a reference value to ascertain the impedance of the patient.

9. A method as defined in claim 4 further defined as measuring the variations in the patient's impedance produced by a physiological functioning of the patient's cardiovascular system and wherein the step of connecting the electrodes is further defined as connecting the electrodes at spaced locations having a desired orientation with respect to the position of a selected portion of the cardiovascular system in the body of the patient.

10. A method as defined in claim 1 further defined as supplying a measuring signal having a frequency of substantially 10–100 kHz to the first electrode.

11. The method as defined in claim 10 further defined as supplying a measuring signal having a frequency of substantially 30 kHz.

12. A method as set forth in claim 1 further defined as supplying a measuring signal comprising a voltage signal to the first electrode.

13. A method as defined in claim 1 further defined as supplying a measuring signal comprising a current signal to the first electrode.

14. A method for measuring impedance characteristics of a patient comprising the steps of:

connecting first, second, and third electrodes to the patient at spaced locations on the skin of the patient;

connecting the third electrode to ground through a grounding impedance;

supplying a periodically varying measuring signal to the first electrode to provide a first electrical signal to the grounding impedance, a characteristic of the first electrical signal being determined by an impedance of the patient;

supplying a periodically varying measuring signal to the second electrode having a predetermined phase relationship to the signal supplied to the first electrode to provide a second electrical signal to the grounding impedance, a characteristic of the second electrical signal being determined by an impedance of the patient; and measuring an electrical characteristic produced at the grounding impedance by the provision of the first and second electrical signals to the grounding impedance to ascertain the impedance characteristics of the patient.

15. A method as defined in claim 14 wherein the measuring step is further defined as measuring the voltage across the grounding impedance, the current flowing through the grounding impedance, or the phase characteristic of the voltage or current resulting from the periodically varying measuring signals.

16. A method as defined in claim 14 wherein the step of supplying a measuring signal to the second electrode is further defined as supplying a measuring signal having a phase property differing from the signal supplied to the first electrode and wherein the measuring step is further defined as measuring a net electrical characteristic produced at the grounding impedance by the first and second signals.

17. A method as defined in claim 16 wherein the step of supplying a measuring signal to the second electrode is further defined as supplying a measuring signal having an opposite phase relationship to the signal supplied to the first electrode.

18. A method as defined in claim 16 for determining a patient's impedance characteristic that varies as a result of the physiological functioning of the patient, wherein the steps of supplying the measuring signals to the first and second electrodes generate first and second electrical signals to the grounding electrode, each, respectively, comprising a carrier signal component and a modulating signal component produced by variations in the impedance characteristics of the patient; and wherein the measuring step is further defined as substantially nulling out the carrier signal components to produce a net electrical characteristic at the grounding impedance resulting from the modulating signal components indicative of the impedance characteristics of the patient.

19. A method as defined in claim 18 further including the step of altering the magnitude of one of the measuring signals to null out the carrier signal components.

20. A method as defined in claim 14 further including the step of altering the magnitude of one of the measuring signals to produce a given net electrical characteristic at the grounding impedance.

21. A method as defined in claim 14 for determining a patient's impedance characteristic that varies as a result of the physiological functioning of the patient, wherein the steps of supplying the measuring signals to the first and second electrodes generate first and second electrical signals to the grounding electrode, each, respectively, comprising a carrier signal component and a modulating signal component produced by variations in the impedance characteristics of the patient; and wherein the measuring step is further defined as substantially nulling out the carrier signal components to produce an electrical characteristic at the grounding impedance resulting from the modulating signal components indicative of the impedance characteristics of the patient.

22. A method as defined in claim 21 further including the step of altering the magnitude of one of the measuring signals to null out the carrier signal components.

23. A method as defined in claim 14 wherein the measuring step is further defined as comparing the electrical characteristic at the grounding impedance to a reference value to ascertain the impedance of the patient.

24. A method as defined in claim 14 for determining changes in impedance produced by the physiological functioning of an internal organ located at a given position in the body of the patient and wherein the step of connecting the electrodes is further defined as connecting the electrodes to the skin at locations that are asymmetric with respect to the position of the internal organ in the body so that the functioning of the organ establishes different impedance characteristics to the first and second measuring signals.

25. A method as defined in claim 24 further defined as a method for measuring the impedance characteristics of a patient resulting from the physiological functioning of the lungs of the patient and wherein the step of connecting the electrodes is further defined as connecting the electrodes to the patient at locations which are asymmetric with respect to the lungs of the patient.

26. A method as defined in claim 25 further defined as a method for determining the impedance characteristics of a patient resulting from the respiratory function of the lungs of the patient.

27. A method as defined in claim 25 wherein the connecting steps are further defined as connecting first, second, and third ECG electrodes to the patient.

28. A method as defined in claim 24 further defined as measuring impedance characteristics produced by a physiological functioning of the patient's cardiovascular system and wherein the step of connecting the electrodes is further defined as connecting the electrodes to the skin at locations which are asymmetric with respect to the position of a selected portion of the cardiovascular system.

29. A method as defined in claim 14 wherein the measuring step is further defined as measuring an electrical voltage characteristic produced at the grounding impedance.

30. A method as defined in claim 14 further defined as supplying a measuring signals having a frequency of substantially 10–100 kHz to the first and second electrodes.

31. A method as defined in claim 14 further defined as supplying a measuring signals having a frequency of substantially 30 kHz.

32. A method as defined in claim 14 further defined as supplying measuring signals comprising voltage signals to the first and second electrodes.

33. A method as defined in claim 14 further defined as supplying measuring signals comprising current signals to the first and second electrodes.

34. A method as defined in claim 14 further including the steps of connecting at least one additional electrode to the skin of the patient, supplying a periodically varying measuring signal to said additional electrode to provide an additional electrical signal, and measuring an electrical property produced in the grounding impedance by the provision of the first, second, and additional electrical signals to the grounding impedance to ascertain the impedance characteristics of the patient.

35. A method as defined in claim 34 further defined as connecting at least one additional electrode corresponding to a first electrode and at least one additional electrode corresponding to a second electrode to the skin of the patient.

36. A method for measuring impedance characteristics of a patient comprising the steps of:
   connecting first and second electrodes to the patient at spaced locations on the skin of the patient;
   connecting the first electrode to ground through a grounding impedance;
   supplying a periodically varying measuring signal to the first electrode to provide an electrical signal to the first electrode; and
   measuring an electrical characteristic produced at the second electrode to ascertain the impedance characteristics of the patient.

37. A method as defined in claim 36, wherein the connecting step is further defined as additionally connecting a third electrode to the patient at a location on the skin of the patient spaced from the first and second electrodes and wherein said measuring step is further defined as measuring an electrical characteristic produced at said third electrode for measuring the impedance characteristics of the patient from the electrical characteristics produced at said second and third electrodes.

38. A method for measuring impedance characteristics of a patient comprising the steps of:
   connecting first and second electrodes to the patient at spaced locations on the skin of the patient;
   connecting a third electrode on the skin of the patient to form an electrocardiographic common electrode;
   providing a common mode drive signal to said third electrode;
   supplying a periodically varying impedance measuring signal to the common mode drive signal; and
   measuring an electrical property produced at at least one of said first and second electrodes to ascertain the impedance characteristics of the patient.

* * * * *

UNITED STATES PATENT AND TRADEMARK OFFICE
CERTIFICATE OF CORRECTION

PATENT NO. : 5,879,308
DATED : March 9, 1999
INVENTOR(S) : Rasanen

It is certified that error appears in the above-indentified patent and that said Letters Patent is hereby corrected as shown below:

On the title page, item:

[30] Foreign Application Priority Data
    952587    Finland    5/26/95

Signed and Sealed this

Eleventh Day of July, 2000

Attest:

Q. TODD DICKINSON

*Attesting Officer*     *Director of Patents and Trademarks*